US007015204B1

(12) United States Patent
Granstein (10) Patent No.: US 7,015,204 B1
(45) Date of Patent: Mar. 21, 2006

(54) PROTECTIVE IMMUNITY OR IMMUNOLOGICAL TOLERANCE INDUCED WITH RNA PARTICULARLY TOTAL CELLULAR RNA

(75) Inventor: Richard D. Granstein, New York, NY (US)

(73) Assignee: Cornell Research Foundation, Inc., Ithaca, NY (US)

( * ) Notice: Subject to any disclaimer, the term of this patent is extended or adjusted under 35 U.S.C. 154(b) by 0 days.

(21) Appl. No.: 09/679,776

(22) Filed: Oct. 5, 2000

Related U.S. Application Data

(60) Provisional application No. 60/198,145, filed on Apr. 17, 2000, provisional application No. 60/158,998, filed on Oct. 7, 1999.

(51) Int. Cl.
*A61K 48/00* (2006.01)
*A01N 63/00* (2006.01)
*C07H 21/04* (2006.01)

(52) U.S. Cl. .................... 514/44; 424/93.2; 424/93.21; 536/23.1

(58) Field of Classification Search ............ 424/93.21; 514/44; 536/23.1
See application file for complete search history.

(56) References Cited

U.S. PATENT DOCUMENTS

| | | | |
|---|---|---|---|
| 5,853,719 A | 12/1998 | Nair et al. ................ | 424/93.21 |
| 6,110,898 A * | 8/2000 | Malone et al. ................. | 514/44 |
| 6,306,388 B1 * | 10/2001 | Nair et al. ................ | 424/93.21 |
| 6,403,080 B1 * | 6/2002 | Segal ......................... | 424/93.1 |

OTHER PUBLICATIONS

W Zhang et al., Human Gene Therapy, "Enhanced Therapeutic Efficacy of Tumor RNA-Pulsed Dendritic Cells after Genetic Modification with Lymphotactin," May 1999, 10:1151-1161.*
B Bodey et al., Anticancer Research, "Failure of Cancer Vaccines: The Significant Limitations of this Approach to Immunotherapy," 2000, 20:2665-2676.*
SL Eck et al., Goodman & Gilman's The Pharmacological Basis of Therapeutics, "Scope of Gene Therapy,"1995, 9th Ed., Chap. 5, pp. 77-101.*
DA Mitchell et al., Current Opinion in Molecular Therapeutics, "RNA transfected dendritic cells as cancer vaccines," Apr. 2000, 2 (2): 176-181.*
Ashley et al, J Exp Med 1997 Oct;186:1177-82.*
Beissert et al , J Immunol 1995;154:1280-86.*
Corny et al, Cancer Rees 1995;55:1397-1400.*
Yu & Restifo, J Clin Invest 2002 Aug;110:289-94.*
Restifo et al, (1993) J. Immunother., vol. 14, pp. 182-.*
Strugnell et al, Immunl Cell Biol 1997;75:364-69.*
Game et al, Wien Klin Wochenschr 2001;113:832-38.*
Platt et al, Nat Biotech 2002 Mar;20(3)231-2.*
Kalden et al, Advances in Immunology, 1998;68:333-418.*
Janeway et al, Chapter 13, Immunobiology 2001.*
Ashley et al., J. Exp. Med. 186: 1177-1182 (1997).
Boczkowski et al., J. Exp. Med., 184: 465-472 (1996).
Gilboa et al., Cancer Immunol. Immunother. 46: 82-87 (1998).
Nair et al., Nature Biotechnology, 16: 364-369 (1998).
Qui et al., Gene Therapy, 3: 262-268 (1996).
Wolff et al., Science, 247: 1465-1468 (1990).

* cited by examiner

*Primary Examiner*—Q. Janice Li
(74) *Attorney, Agent, or Firm*—Darby & Darby (57) ABSTRACT

Effective anti-tumor immunity is induced in mice utilizing RNA-pulsed epidermal cells (EC) for in vivo immunization or by injecting RNA intradermally into naïve mice. A vaccine comprising total cell RNA and a pharmaceutically acceptable carrier for inducing an immune response to reduce or prevent the occurrence of a tumor.

4 Claims, 3 Drawing Sheets

PROTECTIVE IMMUNITY OR IMMUNOLOGICAL TOLERANCE INDUCED WITH RNA PARTICULARLY TOTAL CELLULAR RNA

This invention claims priority of U.S. Application Ser. No. 60/158,998, filed Oct. 7, 1999 and is related to the subject matter of 60/198,145 filed Apr. 17, 2000, which is hereby incorporated by reference in its entirety.

The research leading to this invention was supported in part by NIH R01 AR40667. Thus the U.S. Government may have certain rights in this invention.

FIELD OF THE INVENTION

The present invention relates to methods for treating and preventing tumor growth or pathogen infection in a patient, and for inducing immune tolerance to an antigen, such as an autoantigen, allergen, or transplant tissue.

BACKGROUND OF THE INVENTION

Immunization

Tumor RNA has been used to induce immunity to tumors as an alternative to using tumor derived antigens, tumor extracts (unfractionated) and whole tumor cells. However, only a limited number of defined tumor antigens exist and these antigens are dubious candidates for inducing immune responses. Vaccination with unfractionated tumor material may lead to an increased risk of inducing autoimmune responses and disease.

The use of RNA has certain advantages compared to genetic immunization with DNA. First, there is no danger of incorporation of RNA into the host genome. Second, if total cellular RNA or total messenger RNA is employed for immunization, for example against tumors, it is not necessary to know the nature of the putative tumor-associated antigens. To date, antigen presenting cells (APCs) have been utilized to deliver RNA to the immune system to induce an immune response.

Lymphoid dendritic cells (DCs) exposed in vitro to RNA can be used as antigen presenting cells (APCs) to induce immunity in naïve mice against antigens encoded for by the RNA employed. These include the use of dendritic cells modified to carry tumor RNA for immunization against tumors. Human DCs transfected with RNA encoding a specific tumor associated antigen, carcinoembryonic antigen (CEA) stimulated a potent primary CD8+ CTL response the specific CEA antigen in vitro (Nair et al., Nature Biotechnology, 1998, 16:364–369). Dendritic cell based vaccines pulsed with either B16/F10 murine tumor extract or tumor RNA induced B 16 specific cytotoxic T lymphocytes (CTL) responses (Ashley et al. J. Exp. Med., 1997, 186(7): 1177–1182). Such responses were found to be equal to or more efficient than those elicited by peptide pulsed DCs (Boczkowski et al., J. Exp. Med., 1996, 184:465–472).

Epidermal cells (EC) enriched for Langerhans cell (LC) content have been used as APCs to present a soluble extract of tumor cells as a source of tumor-associated antigens (TAA) for induction of anti-tumor immunity in naïve mice (Grabbe S, et al., J Immunol, 1991;146:3656; Beissert S, et al., J Immunol 1995;154:1280; Grabbe S, et al. J Leukoc Biol 1992;52:209–17; Grabbe S, et al,. J Invest Dermatol 1994;102:67–73; Grabbe S, et al., J. Leukoc Biol 1994;55: 695–701). These studies demonstrated that LC were crucial for the ability of EC populations to induce anti-tumor immunity in this manner. It was also demonstrated that the ability of EC to induce immunity was genetically restricted and tumor-specific. Additionally, pre-exposure of the epidermal cell population to GM-CSF was necessary for efficient induction of anti-tumor immunity in this system.

Two to four percent of the EC population consists of LC which are known professional dendritic antigen-presenting cells (Grabbe S, et al., 1991 supra; Beissert S, et al., supra). LC are relatively immature in situ (Inaba K, et al., J. Exp. Med. 1986; 164:605–13; Witmer-Pack MD, et al. J. Exp. Med. 1987;166:1484–98; Romani N, et al. J. Exp. Med. 1989; 169:1169–78). It is believed that after taking up antigen, they migrate through afferent lymphatics to regional lymph nodes where, under the conditions of the microenvironment within the lymph node, they undergo maturation, upregulate their expression of costimulatory molecules and are able to prime lymphocytes for induction of immunity. Dendritic antigen-presenting cells also reside within the dermis (Nestle and Nickoloff, Adv. Exp. Med. Biol., 1995, 378: 111–116). These cells have a somewhat different phenotype than LC and less is known about their biology. However, they have been shown to be capable of presenting certain types of antigens.

Delivery of naked RNA molecules has been reported for purposes of transgenic expression. However, these methods are limited in that they are cell and tissue specific, have low transfection efficiency and lengthy transduction times (Qiu, P. et al., Gene Therapy, 1996, 3: 262–268). In vivo injection of RNA and DNA molecules has been demonstrated in muscle tissues (Wolfe JA, et al., Science, 1990, 247 1465–1468). Qiu et al has developed a gene gun system to propel RNA- and DNA-coated gold particles into a number of cell and tissue types (Qiu, P. et al., supra). A series of bombardments of the particle-bound mRNA into mouse epidermis cells produced antibodies against the expression product of the delivered mRNA. However, the ability to elicit an antibody response does not establish protective immunity.

Direct delivery of tumor RNA in vivo, or even to epidermal cells ex vivo, to induce an immune response has not been reported. Immunizations with tumor extract alone or tumor RNA alone (not using DCs) did not protect against subsequent challenge with the tumor cells (Ashley et al. J. Exp. Med., 1997, 186(7): 1177–1182).

Thus it would be advantageous to provide an efficient and effective method of inducing an anti-tumor immune response by direct or ex vivo intra-epidermal administration of mRNA that does not require the time consuming and costly procedures involved in generating autologous dendritic cells for immunization ex vivo. It would further be advantageous to provide a method of inducing an immune response to a tumor antigen that will not be limited to a specific cell type or specific antigen or which would induce an undesired autoimmune response.

Tolerance

Many approaches have been employed to achieve tolerance to allografts. Bone marrow transplantation to create a chimera with donor-derived lymphocytes expressing tolerance to both host and donor antigens has been employed in experimental models (Sharabi and Sachs, J. Exp. Med. 1989, 169:493; Cobbold et al., Nature, 1986, 323:164; Schwartz et al., J. Immunol. 1987, 138:460). Several limitations exist to this approach. Of particular significance, fully allogeneic bone marrow chimera animals are immunocompromised (Bradley et al., J. Exp. Med. 1982, 156:1650). Secondly, there is a very significant risk of graft vs. host disease (Martin et al, Adv. Immunol. 1987, 40:379). Attempts have been made to overcome those problems through the use of T cell-depleted syngeneic marrow along with T cell-depleted allogeneic marrow for creation of the chimeric state.

A second means of induced intolerance is to inject donor cells into the thymus with subsequent production of tolerant T cells (Herold et al., J. Exp. Med. 1992, 176:1107; Ohzato and Monaco, Transplantation 1992, 54:1090). This technique must be coupled with ablation of the previous immune system. Another technique that has been employed is the modification of antigen presenting cells in a manner rendering them capable of induced intolerance (Faustman et al., Proc. Natl. Acad. Sci. USA 1981, 78:5156; Rostmgard et al., Hum. Immunol. 1990, 28:153; Hardy et al., Ann. Surg. 1994, 200:441; Deeg, Transplantation 1988, 45:845). There are relatively little data on the long-term success of this approach.

Techniques have also been employed to block costimulatory molecules and other molecules involved in lymphocyte/APC interactions to induced tolerance (Dai and Lakkis, Curr. Opin. Immunol. 1999, 11:504; Hong and Kahan, Semin. Nephr. 2000, 20:125; Ratts et al., Int. Immunol. 1999, 11:1889; Van Gool et al., 1999, Eur. J. Immunol. 29:2367). There is considerable interest in this technology and it is an area of active investigation. This technique may have the promise of inducing anergy in peripheral T cells.

Peripheral tolerance induced by intravenous injection or donor cells is well known (Singal et al., Br. J. Haematol. 1985, 61:595; Miller and Phillips, J. Immunol. 1976, 117: 1913; Sheng-Tanner and Miller, J. Exp. Med. 1992, 176: 407; Lagaaij et al., N. Engl. J. Jed. 1989, 321:701; Salgar et al., J. Leukoc. Biol. 1999, 66:310). It is believed that specific down-regulation of the immune response to donor antigens plays a role in this effect.

New strategies to induce immunologic tolerance may be of considerable use in several areas of medicine. First, the induction of tolerance to alloantigens may be of utility in allotransplantation. In this setting, one could envision induction of tolerance to appropriate, alloantigens prior to transplantation of an allogeneic organ with subsequent acceptance by the host. Another area of interest would be induced tolerance to potential allergens prior to exposure or induction of tolerance to allergens to which an individual is already sensitive. Induction of tolerance to protein antigens has been demonstrated by intravenous administration of antigen (Hillard et al., Exp. Mol. Pathol. 2000, 68:29; Bercovivi et al., Eur. J. Immunol. 1999, 29:345; Rossi et al., Scand. J. Immunol. 1999, 50:177), by oral administration of antigens (revied in Friedman et al., Chem. Imunol. 1994, 58:259) and by intranasal administration of antigens (Rossi et al., supra) in different experimental models. However, there remains a need in the art to identify other methods for developing tolerance to autoantigens, transplanted tissues, and allergens.

SUMMARY OF THE INVENTION

The present invention provides a method of inducing an immune response to a tumor or pathogenic microorganism comprising administering to cutaneous cells of a recipient total cellular RNA in an amount effective to reduce or inhibit the growth of the tumor or microorganism.

In a preferred embodiment of the invention, the total cellular RNA is administered directly into the dermis of the recipient. Accordingly, the present invention provides a method of administering total tumor RNA to generate an immune response wherein the total tumor RNA is injected intradermally, in vivo. Similarly, using pathogen-derived RNA, pathogen infection can be reduced or inhibited.

In another embodiment, the invention provides a method of inducing an immune response to a tumor via immunization with epidermal cells (EC) pulsed with total cellular RNA ex vivo. EC contain Langerhans cells (LC) which may be activated by exposure to GM-CSF. The EC's can be modified by exposure to total cellular RNA derived from a malignant tumor or a pathogen. These cells can be transplanted to the recipient to immunize against the tumor or microorganism.

In another aspect, the invention provides a vaccine comprising immunogenic total cellular RNA and an adjuvant acceptable for use in a human.

In yet another aspect, the invention provides a pharmaceutical composition comprising total cellular RNA and a pharmaceutical carrier. In one embodiment of this aspect of the invention, the total cellular RNA is tumor cell RNA. In another embodiment, the total cellular RNA is derived from a pathogen, for example, a bacterium or virus.

The present invention, in an alternative embodiment, provides a method of inducing immune tolerance to an antigen. This method comprises administering antigen RNA in an amount effective to elicit immune tolerance against the antigen through a tolerization route of administration. Tolerization routes of administration include intravenously, orally, or intranasally.

The invention also provides a related pharmaceutical composition for inducing immune tolerance to an antigen, which composition comprises antigen RNA and a pharmaceutical carrier, which pharmaceutical carrier is suitable for in vivo delivery to a human.

In the tolerization methods and pharmaceutical compositions of the invention, the RNA can be total cellular RNA from tissues containing the antigen, total cellular mRNA from tissues containing the antigen, or mRNA encoding the antigen. Preferred antigens include autoantigens, transplant antigens, and allergens.

The present invention is further explained and exemplified in the following Drawings, Detailed Description and Example.

BRIEF DESCRIPTION OF THE DRAWINGS

Deletion of I-A$^+$ cells prevents induction of immunity by RNA pulsed EC. Mean tumor growth over time was measured in mice that received three consecutive immunizations at weekly intervals with EC treated with anti-I-A antibodies and complement followed by pulsing with S1509a RNA (filled triangle), EC treated with anti I-A antibodies and complement without RNA pulsing (clear circle), EC treated with complement alone followed by RNA pulsing (filled circle), EC treated with antibodies to I-A alone followed by RNA pulsing (clear triangle), and EC pulsed with medium alone (square). Mice were challenged with live S1509a tumor cells one week after the last immunization. N=5 in all groups. A vs. C, D: $p<0.004$. A vs. B, E: NS.

FIG. 6 is a graph illustrating inhibition of tumor growth by treatment of animals given tumor prior to immunization. Groups of mice were inoculated with live S1509a tumor cells subcutaneously. Twenty-four hours later, mice were immunized three times at 24 hour intervals with 10 $\mu$g of total cellular RNA from S1509a cells at each of two sites (open circle), total cellular RNA from the NS cell line (filled squares), the TAA preparation (clear triangles) or medium alone (clear squares). This immunization scheme was then repeated every 48 hours for an additional three immunizations. N=5 in all groups. A vs. B, NS. A vs. C, $p<0.007$. A vs. D, $p<0.0078$.

DETAILED DESCRIPTION OF THE INVENTION

The invention advantageously provides for modulating immune responses by administering antigen RNA. In one aspect, the invention provides immunotherapy against tumors and pathogens using antigen-specific RNA, particularly total cellular RNA or total cellular mRNA. Effective immunization using total cellular RNA can be effected through direct in vivo intradermal injection of RNA or through administration of epidermal cells which have been modified with total cellular RNA.

Alternatively, the invention provides for inducing immune tolerance to an antigen by administering RNA for the antigen via a tolerization route.

The present invention provides a method for preparing vaccines and compositions and medicaments based thereon advantageously using antigen-specific RNA, especially total cellular RNA, or total cellular mRNA from cells against which immunity or tolerization is desired, e.g., tumor cells or derived from pathogens (for immunity), or autoantigens, allergens, and transplant cells (for tolerance).

The present invention is based, in part on the unexpected discovery that epidermal cells can be used as effective antigen presenting cells in vivo and ex vivo. A murine model of human cancer suggests that immunization using total cellular RNA effectively inhibits tumor growth upon challenge with live tumor cells. In this model, total cellular RNA was isolated from the S1509a spindle cell tumor and used to pulse CAF, EC enriched for Langerhans cell content and pre-exposed to GM-CSF. These cells were then injected subcutaneously into naïve CAF, mice three times at weekly intervals, followed by challenge with living S1509a cells. Tumor growth was significantly less in vaccine-treated animals than in control animals immunized in an identical fashion but with irrelevant RNA, or in the case in which S1509a RNA was digested with RNase prior to pulsing of the EC. RNase treatment prevented the development of immunity.

It has also been found that direct administration of tumor RNA into the skin effectively induces anti-tumor immunity. In particular, evidence shows that intradermal injection of S1509a RNA into naïve mice three times at weekly intervals induced immunity to challenge with the tumor. Digestion of S1509a RNA with RNase prior to intradermal injection prevented development of immunity in this system. Thus, effective anti-tumor immunity can be induced utilizing RNA-pulsed EC for ex vivo immunization or by injecting RNA intradermally in vivo into naïve mice.

It is believed, without being bound to any particular theory, that using cutaneous antigen-presenting cells, RNA diffuses across the basement membrane zone of the skin, cutaneous antigen presenting, which may be LCs, take up RNA, translates it in situ and presents relevant antigens for induction of in vivo immunity. Thus, effective immunity is induced by intradermal injection of total cellular RNA from a tumor or pathogenic microorganism.

Ex vivo epidermal RNA vaccination provides the benefits obtained with RNA vaccination. Further, using epidermal cells as antigen presenting cells advantageously avoids the time-consuming and costly procedures involved in generating autologous dendritic cells, e.g., from blood or epidermis.

The present invention is further based on the observation that administration of total cellular RNA from the S1509a tumor intravenously induces tolerance to subsequent immunization with that tumor.

Induction of tolerance in this manner can be accomplished with total cellular RNA, for example, from an allogeneic cell or cells obtained from an organ to be transplanted to a subject; cells from an allergenic organism such as a stinging insect (specifically venom sac RNA), plant (specifically pollen RNA), animal (specifically saliva gland RNA), or mite; cells from an autoantigen or target tissue of an autoimmune response (e.g., nervous tissue in multiple sclerosis, chondrocytes in rheumatoid arthritis, etc); or specific messenger RNA that codes for a protein from one of the foregoing tissues or cells to which it is desirable to induce tolerance. The use of RNA, instead of protein antigens, offers a number of advantages. First, the use of total cellular RNA obviates the need to know the precise antigen or antigens that are relevant for induction of tolerance. Secondly, because RNA can be easily amplified, only a small sample of the material is necessary to obtain RNA for tolerization.

While in accordance with the present invention the intravenous (iv) route of administration effected tolerization, as exemplified, administration of RNA by other routes known to favor tolerance (i.e., intranasal or oral) is also expected to be effective.

Preferably, this technique allows for more profound induction of tolerance, compared to other techniques such as intravenous administration of protein antigen, exposure to antigen in the presence of agents known to block effective co-stimulation, etc. This can be shown by direct comparison.

Although not intending to be limited to any particular theory or mechanism, the molecular mechanisms by which tolerance to antigens or tissues delivered by RNA may result from uptake of the RNA by appropriate cells, probably in the spleen, with translation and presentation of peptides derived from the RNA for induction of tolerogenic mechanisms.

Definitions

The term "immune response" has its ordinary meaning in the art, and includes both humoral and cellular immunity. Immune response can manifest as one or more of development of anti-tumor or anti-tumor antigen antibodies; expansion of tumor-specific T lymphocytes, which can be deleted by various proliferation or cytokine production assays in vitro; increase in tumor infiltrating-lymphocytes (TILs); development of an anti-tumor or anti-tumor antigen delayed-type hypersensitivity (DTH) response as detected by skin-testing; suppression of tumor growth; tumor reduction; reduction or elimination of metastases; increased time to regression; increased time of tumor-free survival; and increased time of survival. Similar end-points are relevant to microorganism infection as well, e.g., clearance and survival. Depending on the relevant circumstances, any one or more of these factors can be evaluated to ascertain efficacy of the total RNA vaccine. Examples of these assays are found in the literature, including U.S. Pat. No. 5,484,596 (antibody response; DTH); U.S. Pat. No. 5,290,551 (DTH; survival); International Patent Publication WO96/40173 (T cell responses, including proliferation, cytokine production, and TILs); and Paul, *Fundamental Immunology, Third Edition*, Raven Press Ltd: New York.

"Immunologically effective" means that a process or composition elicits an immune response.

As used herein, the term "pathogen" refers to a tumor or to a pathogenic microorganism. Pathogenic microorganisms includes viruses, bacteria, single celled organisms, and parasites. Human immunodeficiency virus (HIV), cytomegalovirus (CMV), herpes virus (HSV), hepatitis A virus (HAV), HBV, HCV, papilloma virus, and human T lymphotrophic virus (HTLV) exemplify pathogenic viruses, without limiting the invention. Similarly, *Streptococcus pneumoniae, Staphylococcus aureus, Enterococcus faceum, Salmonella*, and other bacteria are targets for vaccines of the invention. Single celled organisms include *plasmodium*, trypanisome, amoeba, and the like.

The term "vaccine" refers to a composition that can be used to elicit protective immunity in a recipient. It should be noted that to be effective, a vaccine of the invention can elicit immunity in a portion of the population, as some individuals may fail to mount a robust or protective immune response, or, in some cases, any immune response to the vaccine. This inability may stem from the individual's genetic background or because of an immunodeficiency condition (either acquired or congenital) or immunosuppression (e.g., treatment with immunosuppressive drugs to prevent organ rejection or suppress an autoimmune condition). Efficacy can be established in animal models.

The term "immunotherapy" refers to a treatment regimen based on activation of a pathogen-specific immune response. In the present case, a tumor, virus, bacterium or parasite is considered the pathogen. An anti-tumor vaccine as described herein is a form of immunotherapy. Pulsing epidermal cells with tumor RNA, and activating the cells, preferably with a stimulatory cytokine such as GM-CSF (followed by transplantation into the subject), or in vivo immunization, preferably with such activation, is also a form of immunotherapy.

For purposes of the present invention, the "antigen presenting cell" is a skin cell, for example, an epidermal cell. The RNA is introduced into the epidermal cell, preferably by intradermal direct injection, alternatively by pulsing the cell ex vivo (followed by translation of the pulsed cells), with purified RNA, a substantially pure RNA preparation, or a soluble cell extract.

For purposes of the present invention "total cellular RNA" includes total cellular messenger RNA (mRNA).

The term "cutaneous" is used herein to mean skin which includes but is not limited to, epidermis cells, dermis cells, Langerhans cells, and the like.

The term "intravenous" is used herein to mean injection directly into the veins. Intra arteriole (direct injection to the arteries) will also likely work, but is a much more difficult technique.

The term "protect" is used herein to mean prevent or treat, or both, as appropriate, the occurrence and/or growth of a tumor or microorganism in a subject. Thus, prophylactic administration of the vaccine can protect the recipient subject from initiation of tumor growth, e.g., to prevent onset of cancer, or from infection by the microorganism. Therapeutic administration of the vaccine or immunotherapy can protect the recipient from spread or mestastases of existing tumors, e.g., to treat a disease or disorder such as but not limited to melanomas, breast cancers, bladder cancers, colon cancers, ovarian cancers, pancreatic cancers, prostate cancers, etc., or from persistence of the microorganism.

The term "inhibit" is used herein to mean prevent or suppress the occurrence of tumor growth or to prevent the occurrence of pathogenic disease. The term "reduce" is used herein to mean decrease the number of or the size of tumors in a subject or to decrease the intensity of deleterious or unwanted symptoms that occur as a result of a pathogenic infection.

The term "tolerize" is used herein the man induce immunological tolerance. It is the avoidance of or suppression of a specific immune response. Immunological tolerance can be used to prevent or ameliorate transplant rejection, autoimmunity, allergic reaction, or another undesirable immune response.

An "undesirable immune response" includes, without limitation, acute and chronic transplant rejection (host-versus-graft disease), graft-versus-host disease, and allergy. Undesirable immune responses also specifically includes an autoimmune disease. An "autoimmune disease" is a malfunction of the immune system, i.e., a pathological condition in which the immune system of a mammal (including a human) ceases or fails to recognize self (i.e., autologous antigens) and as a result treats these substances self antigens as if they were foreign antigens and mounts an immune response against them. Typically, autoimmune diseases that are organ-or tissue-specific involve, in whole or in part, priming or activation of autoreactive cells expressing the Th2 phenotype (rather than the Th2 phenotype, which is expressed by regulatory T-cells). Non-limiting examples of autoimmune disease include multiple sclerosis (MS), Type 1 diabetes (IDDM), rheumatoid arthritis (RA), urenothritis (UR), systemic lupus erythematosis, and autoimmune thyroidites thyroiditis (AT).

The term "ex vivo" is used herein to mean the total cell RNA is placed into cells outside of the animal body, i.e., the epidermal cells are modified with the RNA in vitro and then administered (transplanted) to a subject.

The term "subject" as used herein refers to an animal that supports tumor growth or that otherwise suffers from an undesirable immune response. In particular, the term refers to a human, but also includes domestic animal (canine, feline), laboratory animals (especially murine, racine, rabbit and other rodentia), farm animals (equine, bovine, ovine, caprine, porcine etc.), avian species and wild animals, e.g., in a zoo.

An "adjuvant" is a molecule or composition that potentiates the immune response to an immunogen. An adjuvant is "acceptable for use in a human" when it is pharmaceutically acceptable, as defined below. Examples of adjuvants are provided below.

The various aspects of the invention will be set forth in greater detail in the following sections. This organization into various sections is intended to facilitate understanding of the invention, and is in no way intended to be limiting thereof.

Total Cellular and Antigen-Specific RNA

The total cellular RNA to be used in the present invention may be obtained using a variety of methods e.g., as described in U.S. Pat. No. 5,853,719. It is not necessary that the RNA be in purified form. Preferably the RNA sample is at least 80% and most preferably at least 90% RNA (wt/wt or by mole). The term total cellular RNA includes total messenger RNA (mRNA) or poly-A RNA. To be most effective, total cellular RNA contains mRNA encoding antigens against which an immune response (or, alternatively, immune tolerance) is desired.

Total cell RNA may be obtained, for example, by lysing the cells, e.g., tumor or transplant organ cells, or pathogenic bacteria, or cells containing a pathogenic virus, by homogenization or sonication in suitable buffers, extracting and precipitating the RNA fraction from the cell homogenate. Alternatively, the RNA can be prepared utilizing RNA purification methods known in the art such as guanidinium isothiocyanate methods and/or oligo dT chromatography methods for isolating poly $A^+$ RNA. The RNA containing preparation can be fractionated to decrease the concentration of other components in the preparation for example, lipids, proteins or DNA to enrich the concentration of RNA in the preparation. The preparation can also be treated with proteases or RNase-free Dnases. Total mRNA can be obtained by isolating it on a poly-T column. The dose of total cellular RNA will be in an amount effective to induce an immune response or immune tolerance. Such amount can be readily determined by a skilled physician and will vary with the nature and severity of the condition to be treated. Typical dosage ranges of cellular RNA are from about 1 µg to about 100 µg and depending on the nature and severity of the condition being treated can be adjusted to a range from about 0.1 µg to about 10 mg RNA. Typically a total of 20 µg RNA, in two (2) 10 µg/flank doses can be administered in each animal.

Although it can vary with cell types, $10^6$ cells provide approximately 10 µg RNA. Thus dosages can range from about $10^6$ to about $10^7$ cell equivalents, or can be adjusted for example to about $10^6$ to about $10^8$ cell equivalents per administration.

In order to obtain amounts of RNA sufficient for use in the methods described herein, conventional amplification techniques may be used. Cellular RNA can be reverse transcribed in vitro to produce cDNA for amplification by PCR. The cDNA then is transcribed in vitro to produce tumor RNA.

The RNA may be obtained by isolating RNA from a cultured cell line, for example, S1509a methylcholanthrene-induced fibrosarcoma cell line. The cells are lysed by adding a lysing buffer such as TRIzol Reagent (GIBCO-BRL), and homogenizing by passing the mixture through a pipette several times. Chloroform is added the mixture is shaken and centrifuged. Phase separation of the mixture provides the RNA in the aqueous phase which is removed and the RNA is precipitated with isopropyl alcohol.

In accordance with the present invention there may be employed conventional molecular biology, microbiology, and recombinant nucleic acid techniques within the skill of the art. Such techniques are explained fully in the literature. See, e.g., Sambrook, Fritsch & Maniatis, *Molecular Cloning: A Laboratory Manual*, Second Edition (1989) Cold Spring Harbor Laboratory Press, Cold Spring Harbor, N.Y. (herein "Sambrook et al., 1989"); *DNA Cloning: A Practical Approach*, Volumes I and II (D. N. Glover ed. 1985); *Oligonucleotide Synthesis* (M. J. Gait ed. 1984); *Nucleic Acid Hybridization* [B. D. Hames & S. J. Higgins eds. (1985)]; *Transcription And Translation* [B. D. Hames & S. J. Higgins, eds. (1984)]; *Animal Cell Culture* [R. I. Freshney, ed. (1986)]; *Immobilized Cells And Enzymes* [IRL Press, (1986)]; B. Perbal, *A Practical Guide To Molecular Cloning* (1984); F. M. Ausubel et al. (eds.), *Current Protocols in Molecular Biology*, John Wiley & Sons, Inc. (1994).

Delivering RNA

The epidermal cells can be "transfected" by exogenous or heterologous RNA when such RNA has been introduced inside the cell. The RNA can be introduced into the cells by "pulsing", i.e., incubating the cells with the total cell RNA. Alternatively, the RNA can be introduced in vivo by lipofection, as naked RNA, or with other transfection facilitating agents (peptides, polymers, etc.). Synthetic cationic lipids can be used to prepare liposomes for in vivo transfection of a gene encoding a marker (Felgner, et. al., Proc. Natl. Acad. Sci. U.S.A. 84:7413–7417, 1987; Felgner and Ringold, Science 337:387–388, 1989; see Mackey, et al., Proc. Natl. Acad. Sci. U.S.A. 85:8027–8031, 1988; Ulmer, et al., Science 259:1745–1748, 1993). Useful lipid compounds and compositions for transfer of nucleic acids are described in International Patent Publications WO95/18863 and WO96/17823, and in U.S. Pat. No. 5,459,127. Suitable lipids include DODC, DOPE, CHOL, DMEDA, DDAB, DODAC, DOTAP and DOTMA. Lipids may be chemically coupled to other molecules for the purpose of targeting (see Mackey, et al., supra). Targeted peptides, e.g., hormones or neurotransmitters, and proteins such as antibodies, or non-peptide molecules could be coupled to liposomes chemically.

Other molecules are also useful for facilitating transfection of a nucleic acid in vivo, such as a cationic oligopeptide (e.g., International Patent Publication WO95/21931), peptides derived from DNA binding proteins (e.g., International Patent Publication WO96/25508), or a cationic polymer (e.g., International Patent Publication WO95/21931).

Alternatively, non-viral DNA vectors for gene therapy can be introduced into the desired host cells by methods known in the art, e.g., electroporation, microinjection, cell fusion, DEAE dextran, calcium phosphate precipitation, use of a gene gun (ballistic transfection; see, e.g., U.S. Pat. No. 5,204,253, U.S. Pat. No. 5,853,663, U.S. Pat. No. 5,885,795, and U.S. Pat. No. 5,702,384 and see Sanford, TIB-TECH, 6:299–302, 1988; Fynan et al., Proc. Natl. Acad. Sci. U.S.A., 90:11478–11482, 1993; and Yang et al., Proc. Natl. Acad. Sci. U.S.A., 87:1568–9572, 1990), or use of a DNA vector transporter (see, e.g., Wu, et al., J. Biol. Chem. 267:963–967, 1992; Wu and Wu, J. Biol. Chem. 263: 14621–14624, 1988; Hartmut, et al., Canadian Patent Application No. 2,012,311, filed Mar. 15, 1990; Williams, et al., Proc. Natl. Acad. Sci. USA 88:2726–2730, 1991). Receptor-mediated DNA delivery approaches can also be used (Curiel, et al., Hum. Gene Ther. 3:147–154, 1992; Wu and Wu, J. Biol. Chem. 262:4429–4432, 1987). U.S. Pat. Nos. 5,580, 859 and 5,589,466 disclose delivery of exogenous DNA sequences, free of transfection facilitating agents, in a mammal. Recently, a relatively low voltage, high efficiency in vivo DNA transfer technique, termed electrotransfer, has been described (Mir, et al., C. P. Acad. Sci., 321:893, 1998; WO 99/01157; WO 99/01158; WO 99/01175).

A "tumor-associated antigen"preparation (TAA) used herein is obtained by solubilizing tumor cells. In this unfractionated RNA preparation the tumor antigens may not be specifically identified.

Anti-Tumor and Anti-Microbial Therapy

The present invention provides an immunogenic composition capable of inducing an immune response to challenge by tumor or a microorganism. The immunogenic molecule is total cellular RNA. As used herein, the term immunogenic means that the RNA is capable of eliciting a humoral or cellular immune response, and preferably elicits responses from both facets of the immune system.

The present treatment is suitable for application to a variety of conditions, which benefit from the stimulation and/or inhibition of the immune system. As used herein, the term "pathogen infection" includes diseases and disorders that result from a tumor, or from viral or bacterial infection. It further includes parasite infestation. In addition, for purposes of the present invention as it relates to immunotherapy, the term "infectious disease" includes cancer.

The vaccine of the present invention may be utilized to treat or protect subjects afflicted with conditions manifesting tumors such as but not limited to melanomas, breast cancers, bladder cancers, colon cancers, ovarian cancers, pancreatic cancers, prostate cancers, etc., as set forth above. The method of the present invention may be used to eliminate reduce preexisting mestastases in subjects whose primary tumor has been removed (surgically) or destroyed (chemo/radio therapy); prevent the occurrence of primary tumor growth; treat existing tumor to inhibit reduce growth; and induce regression of existing tumors.

Tumor Cells

The compositions of the present invention are prepared using RNA from tumor cells, e.g., cells obtained from tumors surgically resected in the course of a treatment for a cancer. The tumor cells for use in the present invention may be prepared as follows. Tumors may be processed as described by Berd et al., Cancer Res., 46:2572, 1986, Sato, et al., Cancer Invest., 15:98, 1997, U.S. Pat. No. 5,290,551, or corresponding PCT application WO96/40173, each of which is incorporated herein by reference in its entirety. Briefly, the cells are extracted by dissociation, such as by enzymatic dissociation with collagenase and DNase, by mechanical dissociation in a blender, by teasing with tweezers, using mortar and pestle, cutting into small pieces using a scalpel blade, and the like. With respect to liquid tumors, blood or bone marrow samples may be collected and tumor cells isolated by density gradient centrifugation.

Preferably the cells originate from the type of cancer which is to be treated, and more preferably, from the same patient who is to be treated. The tumor cells may be, and are not limited to, autologous cells dissociated from biopsy or surgical resection specimens, or from tissue culture of such cells. Nonetheless, allogeneic cells and stem cells are also within the scope of the present invention. In either case, amplification procedures permit preparation of large amounts of tumor cell RNA for vaccination immunotherapy of the tumor.

The ability of the tumor RNA vaccine to reduce or inhibit the formation of tumors in a subject can be determined by measuring the tumor growth over a period of time before during and after immunization, as applicable. Such measurements can be made after surgical excision of the tumor, e.g., by CAT scan, MRI, PET scan, and the like.

In one aspect, the present invention is directed for use in the preparation of tumor cell vaccines for treating cancer, including metastatic and primary cancers. Cancers treatable with the present invention include solid tumors, including carcinomas, and non-solid tumors, including hematologic malignancies. Examples of solid tumors that can be treated according to the invention include sarcomas and carcinomas such as, but not limited to: fibrosarcoma, myxosarcoma, liposarcoma, chondrosarcoma, osteogenic sarcoma, chordoma, angiosarcoma, endotheliosarcoma, lymphangiosarcoma, lymphangioendotheliosarcoma, synovioma, mesothelioma, Ewing's tumor, leiomyosarcoma, rhabdomyosarcoma, colon carcinoma, pancreatic cancer, breast cancer, ovarian cancer, prostate cancer, squamous cell carcinoma, basal cell carcinoma, adenocarcinoma, sweat gland carcinoma, sebaceous gland carcinoma, papillary carcinoma, papillary adenocarcinomas, cystadenocarcinoma, medullary carcinoma, bronchogenic carcinoma, renal cell carcinoma, hepatoma, bile duct carcinoma, choriocarcinoma, seminoma, embryonal carcinoma, Wilms' tumor, cervical cancer, testicular tumor, lung carcinoma, small cell lung carcinoma, bladder carcinoma, epithelial carcinoma, glioma, astrocytoma, medulloblastoma, craniopharyngioma, ependymoma, pinealoma, hemangioblastoma, acoustic neuroma, oligodendroglioma, meningioma, melanoma, neuroblastoma, and retinoblastoma. Hematologic malignancies include leukemias, lymphomas, and multiple myelomas. The following are non-limiting preferred examples of the cancers treatable with the composition and methods of the present invention: melanoma, including stage-4 melanoma; ovarian, including advanced ovarian; leukemia, including and not limited to acute myelogenous leukemia; colon, including colon metastasized to liver; rectal, colorectal, breast, lung, kidney, and prostate cancers. In a specific example, the tumor is a fibrosarcoma.

RNA Vaccines

As used herein, the term "RNA vaccine" refers to a vaccine comprising RNA. It can further include an adjuvant. The term "adjuvant" refers to a compound or mixture that enhances the immune response to an antigen. An adjuvant can serve as a tissue depot that slowly releases the antigen and also as a lymphoid system activator that non-specifically enhances the immune response (Hood, et al., Immunology, Second Ed., 1984, Benjamin/Cummings: Menlo Park, Calif., p. 384). Adjuvants include, but are not limited to, complete Freund's adjuvant, incomplete Freund's adjuvant, saponin, mineral gels such as aluminum hydroxide, surface active substances such as lysolecithin, pluronic polyols, polyanions, peptides, oil or hydrocarbon emulsions, and potentially useful pharmaceutically acceptable human adjuvants such as BCG (bacille Calmetle-Guerin) and *Corynebacterium parvum*.

Alternatively, or in addition, immunostimulatory proteins, as described below, can be provided as an adjuvant or to increase the immune response to a vaccine. Preferably, the adjuvant is pharmaceutically acceptable.

The phrase "pharmaceutically acceptable" refers to molecular entities and compositions that are physiologically tolerable and do not typically produce an allergic or similar untoward reaction, such as gastric upset, dizziness and the like, when administered to a human. Preferably, as used herein, the term "pharmaceutically acceptable" means approved by a regulatory agency of the Federal or a state government or listed in the U.S. Pharmacopeia or other generally recognized pharmacopeia for use in animals, and more particularly in humans. The term "carrier" refers to a diluent, adjuvant, excipient, or vehicle with which the compound is administered. Sterile water or aqueous solution saline solutions and aqueous dextrose and glycerol solutions are preferably employed as carriers, particularly for injectable solutions. Suitable pharmaceutical carriers are described in "Remington's Pharmaceutical Sciences" by E. W. Martin.

Certain adjuvants mentioned above, particularly mineral oils and adjuvants containing mineral oils (e.g., Freund's adjuvant) are not acceptable for use in humans.

Vaccination effectiveness may be enhanced by co-administration of an immunostimulatory molecule (Salgaller and Lodge, J. Surg. Oncol., 1988, 68:122), such as an immunostimulatory, immunopotentiating, or pro-inflammatory cytokine, lymphokine, or chemokine with the vaccine, particularly with a vector vaccine. For example, cytokines or cytokine genes such as interleukin (IL)-1, IL-2, IL-3, IL-4, IL-12, IL-13, granulocyte-macrophage (GM)-colony stimulating factor (CSF) and other colony stimulating factors, macrophage inflammatory factor, Flt3 ligand (Lyman, Curr. Opin. Hematol., 1998, 5:192), CD40 ligand, as well as some key costimulatory molecules or their genes (e.g., B7.1, B7.2) can be used. These immunostimulatory molecules can be delivered systemically or locally as proteins or by expression of a vector that codes for expression of the molecule. The techniques described above for delivery of the immunogenic polypeptide can also be employed for the immunostimulatory molecules.

Tolerization

As noted above, the present invention provides isolated or total cellular RNA for eliciting immune tolerance to an antigen, e.g., an autoantigen, allergen, or transplant tissue.

Examples of sources of autoantigens include, but are by no means limited to, thyroid (associated with various thyroiditises, such as Hashimoto's disease), pancrease (especially beta cells of the islets of Langerhans; associated with insulin-dependent diabetes mellitus), heart tissue (associated with rheumatic fever), nerve tissue (associated with multiple sclerosis), joint tissue/chondrocytes (associated rheumatoid arthritis), to mention a few sources of total or antigen-specific RNA (and the autoimmune diseases with which they are associated).

Examples of allergens include ragweed pollen, tree pollen, vespid (wasp) venom, apid (bee) venom, dust mites, cat dander, dog dander, and the like. (Note that animal dander typically causes allergy because of the presence of saliva allergens). Whole allergens (insects, mites, plants), or specific cells or tissues from allergens (pollen, venom sacs, salivary cells) can be used to generate total cell RNA or antigen-specific RNA. The use of total cellular RNA ensures that the allergen-specific RNA (or RNAs, as often there are multiple allergenic components from a single source) will be present in the preparation. Moreover, induction of tolerance to total cellular RNA ensures that new allergens will not elicit allergic responses.

Examples of transplant tissues include organs, such as heart, lungs, liver, kidney, pancreas (especially beta islet cells); tissues, such as skin; and blood cells, such as platelets, lymphocytes, leukocytes, and red blood cells (which can be tolerized with reticulocyte RNA).

Tolerization to an antigen (or total RNA antigens) can depend on the route of administration of the tolerigen. Intravenous administration is preferred, but other routes of administration are available. For example, oral and intranasal administration of protein antigens elicits immune tolerance. By appropriate formulation of the antigen RNAs, these routes can also be used with RNA.

EXAMPLES

The present invention will be better understood by reference to the following examples, which are provided by way of exemplification and are not intended to limit the invention. The results described below, although achieved in mice, are predictive of results in other mammals, especially humans.

Example 1

Ex Vivo Immune Therapy in Cutaneous Cells

Mice. Six to 12-wk-old CAF, (H-$2^a$) female mice were obtained from the Jackson Laboratories (Bar Harbor, Me.). Mice were housed in the animal facility of the Weill Medical College of Cornell University, New York, N.Y.

Tumor and cell line. The S1509a methylcholanthrene-induced fibrosarcoma cell line, originally derived from A/J mice, has been described (Fujimoto S. et al., Immunol Commun 1975, 4: 201). This cell line was maintained in tissue culture at 37° C. and 5% $CO_2$ in RPMI 1640 supplemented with 10% heat-inactivated FCS (Gibco Laboratories, Grand Island, N.Y.), 100 U/ml penicillin, 100 (g/ml streptomycin, 0.1 mM essential and nonessential amino acids, 2 mM L-glutamine, 1 mM sodium pyruvate and 0.01 M HEPES buffer ("complete medium"). The NS cell line has also been described. It was propagated in complete medium.

Reagents. For selective cell deletion, the following monoclonal antibodies were used: Anti-Thy 1.2 (Sigma, St. Louis, Mo.), anti-I-$A^d$ (PharMingen, San Diego, Calif.) and anti-I-$A^k$ (PharMingen, San Diego, Calif.). Low-toxicity rabbit complement was obtained from Cedarlane Laboratories (Hornby, Ontario, Canada). Enzymes included dispase (Boehringer Mannheim, Indianapolis, Ind.), DNase and trypsin (both from Sigma Chemical Co., St. Louis, Mo.).

Preparation of RNA. Total RNA was isolated by TRIzol Reagent (GIBCO-BRL, Gaithersburg, Md.). Cells were lysed directly in culture flasks by adding 10 ml of TRIzol Reagent to 75 $cm^2$ flasks followed by passing the cell lysate several times through a pipette. The homogenized samples were incubated for 5 minutes at 15° C. to permit the complete dissociation of nucleoprotein complexes. Two-tenths ml of chloroform per 1 ml of TRIzol Reagent were then added, and tubes were shaken vigorously by hand for 15 seconds followed by incubation at 15° C. for 2 minutes. Samples were then centrifuged at 12,000×g for 15 minutes at 4° C. The mixture separated into a lower red phenol-chloroform phase, an interphase, and a colorless upper aqueous phase. RNA remained exclusively in the aqueous phase. The aqueous phase was then transferred to a fresh tube and precipitated with 0.5 ml of isopropyl alcohol per 1 ml of TRIzol Reagent used for the initial homogenization. The sample was incubated at 15° C. for 10 min and then centrifuged at 12,000×g for 10 min at 4° C. The RNA pellets were then washed once with 75% ethanol and centrifuged at 7,500×g for 5 min at 4° C. The RNA pellets were air-dried, dissolved in RNase-free water and incubated for 10 minutes at 55° C. Total RNA was quantitated by measuring OD at 260 and 280 nm. The OD 260/280 ratio was 1.8–1.9 in all experiments. Total RNA was stored at −70° C.

Preparation of TAA. S1509a cells were resuspended at $1\times10^7$ cells/ml in complete medium and disrupted by four freeze-thaw cycles. The tumor cell fragments were spun at 600×g for 10 min, the supernatant collected and spun again at 13,000×g for 60 min. This supernatant was used as a source of soluble TAA.

Preparation of EC. EC were prepared by using a modification of a standard protocol (Grabbe S et al., J Immunol, 1991, 146:3656). Briefly, truncal skins of shaved and chemically depilated (Neet, Whitehall Laboratories, New York, N.Y.) mice were removed and depleted of subcutaneous fat and panniculus carnosus. The skins were floated dermis-side-down on 1.5 U/ml dispase in $CA^{2+}/Mg^{2+}$-free PBS for 35 to 45 min at 37° C., and epidermal sheets were collected and dissociated by incubation in 0.05% trypsin and 80 (g/ml DNase in $CA^{2+}/Mg^{2+}$-free PBS for 15 min at 37° C. under continuous gentle agitation, filtered through nylon gauze (Nytex: Tetko, Elmsford, N.Y.), and washed in HBSS supplemented with 5% FCS.

Thy-1-bearing cells were deleted by incubation in anti-Thy-1.2 mAb solution at 1:2000 for 30 min on ice, washing, and subsequent incubation in low-toxicity rabbit C at 1:30 in PBS for 35 min at 37° C. I-A-expressing cells were deleted in the same manner except that a 50:50 mixture of anti I-$A^k$ and anti-I-$A^d$ (each at 5 (g/ml) were substituted for anti-Thy 1.2. After washing 3 times, dead cells were removed by treatment with 0.05% trypsin and 80 (g/ml DNase in PBS for 10 min at 37° C.

Pulsing of EC with RNA or TAA. EC were washed 3 times with serum-free Opi-MEM medium (GIBCOBRL), resuspended in Opi-MEM at 5×10 cells/ml and placed in a 50 ml polypropylene tube. Total RNA and DOTAP (GIBCO-BRL) were diluted in Opi-MEM medium and incubated at room temperature for 20 minutes. The ratio of total RNA to DOTAP was 1:2. The complex was then added to the same volume of EC suspension and incubated at 37° C. with occasional agitation for 4 hours. The final concentration of total RNA was 30 μg/ml and that of DOTAP was 60 μg/ml. EC were also incubated for 4 h with TAA or in complete medium alone in some experiments. After incubation, the EC were washed 4 times to remove any remaining extracellular RNA or TAA.

Immunization protocol. EC were incubated for 16 h in 50 U/ml GM-CSF, which has been shown to augment the alloantigen presenting capability of LC (Beissert S et al., J. Immunol. 1997, 159: 92–96). The cells were then washed 3 times and incubated in a solution containing RNA (3 μg/ml), TAA or in complete medium alone for 2 h at 37° C. After incubation, the EC were washed 4 times to remove any remaining extracellular RNA or TAA. Identical numbers of EC for each group ($2\times10^5$) in PBS were then injected s.c. into naïve recipient mice on the lower back. This immunization was repeated at weekly intervals for a total of two to three immunizations.

In some experiments mice were immunized by intradermal administration of total cellular RNA. In these experiments RNA was prepared as above and 10 mg in 0.1 ml PBS was injected intradermally on each flank. This immunization was repeated twice at weekly intervals.

Ribonuclease treatment. In some experiments RNA and/or TAA was treated with RNase prior to pulsing of EC or intradermal injection. In these experiments RNA was treated for 20 min at 37° C. with 2 units of ribonuclease (GIBCO-BRL) per 20 mg RNA. For treatment of TAA, 10 units of RNase was added to 1 ml of TAA preparation followed by culture at 37° C. for 20 min.

Tumor challenge. One week after the last immunization, the mice were challenged with $1\times10^6$ live S1509a cells s.c. on the lower lateral abdomen, i.e., at a different site than that of the immunizations. Tumor growth was scored every 48 h. Data generation and statistical evaluation. Tumor volumes were calculated as the product of the maximal tumor diameter in three perpendicular directions, measured with a Vernier caliper. This method has been confirmed previously to correlate well with the tumor weight (Grabbe S et al., J Immunol, 1991, 146:3656). To evaluate statistic differences between the mean tumor volume in the various experimental groups, the "best-fit" slope of the tumor growth in each animal was determined using Cricket Graph software (version 1.3.2; Criket Software, Malverne, Pa.) on a Macintosh computer, and the significance of differences between the means of the slopes for the groups of interest was tested by the two-tailed Student's t-test for unpaired data.

Figure 1:
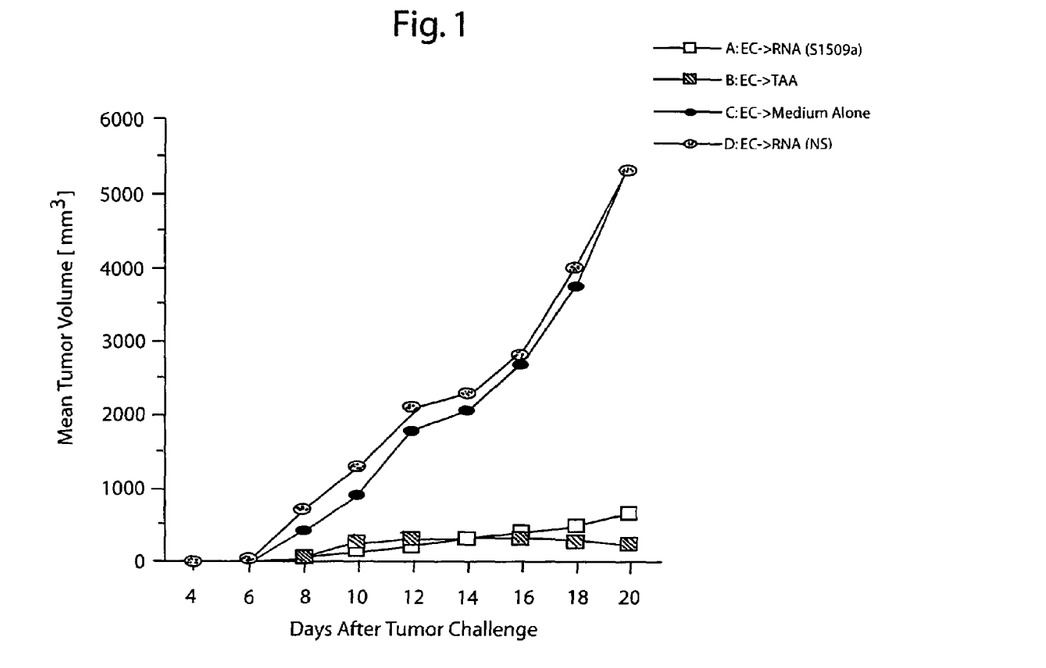
FIG. 1 is a graph showing the effect on tumor growth in mice immunized with EC pulsed with RNA. Mean tumor growth over time was measured in mice that received three consecutive immunizations at weekly intervals with $2 \times 10^5$ EC pulsed with S1509a RNA (filled square), S1509a tumor-associated antigens (TAA) (clear square), medium alone (filled oval) or NS (non tumor) cell line RNA (clear oval). Mice were challenged with live S1509a tumor cells one week after the last immunization. N=5 in all groups. A vs. C, D: $p<0.01$. A vs. B: NS. NS=not significant.

Immunization with RNA-pulsed EC. $CAF_1$ EC were generated, cultured in GM-CSF and pulsed with total cellular RNA. The cells were then washed 4 times and $2\times10^5$ cells injected s.c. into each of 5 naïve $CAF_1$ mice. A second group of naïve mice was immunized in the same manner but RNA from NS cells was substituted for S1509a cell RNA. A third group of mice was immunized with EC pulsed with TAA. A group of negative control animals was immunized with cells treated identically but not pulsed with RNA. Primings were repeated twice at weekly intervals and one week following the last immunization, all mice were challenged by s.c injection with living S1509a cells and tumor growth scored over time. As shown by the data in FIG. 1, mice immunized by EC pulsed with RNA or TAA derived from the S1509a tumor demonstrated little tumor growth while tumors grew progressively in the two other groups. These differences were statistically significant.

Figure 2:
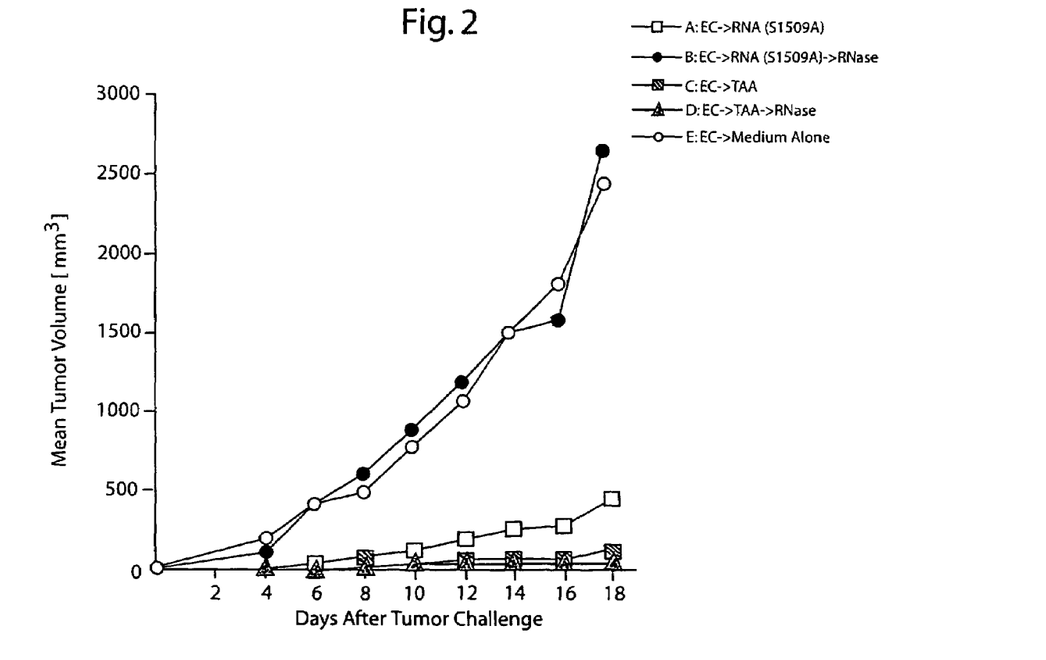
FIG. 2 is a graph illustrating the comparison of the effect on tumor growth in mice immunized with EC pulsed with RNA or RNA treated with RNase. S1509a RNA was treated with RNase prior to EC pulsing. Mean tumor growth over time was measured in mice that were immunized with EC pulsed with S1509a RNA (clear square), S1509a RNA pre-treated with RNase (filled circle), EC pulsed with TAA (filled square), EC pulsed with TAA pre-treated with RNase (triangle) or EC pulsed with medium alone (clear circle). N=5 in all groups. A vs. B, E: $p<0.006$. A vs. C, D: NS.

Effect of RNase treatment of RNA prior to EC pulsing. To confirm that immunization with RNA-pulsed EC does not result from presentation of protein antigens or DNA contaminating the RNA preparation, a group of animals was immunized with EC pulsed with RNA pre-treated with RNase. This group was compared with groups of mice primed with EC pulsed with TAA, EC pulsed with RNA not treated with RNase and EC pulsed with TAA treated with RNase. As shown by the data in FIG. 2, mice primed with EC pulsed with RNA or EC pulsed with TAA showed immunity to challenge with living tumor cells. Mice primed with EC pulsed with TAA that had been pre-treated with RNase also demonstrated full immunity against challenge with the tumor. However, mice immunized with EC pulsed with RNA that had been treated with RNase failed to show immunity; the tumors grew progressively in this group.

Figure 3:
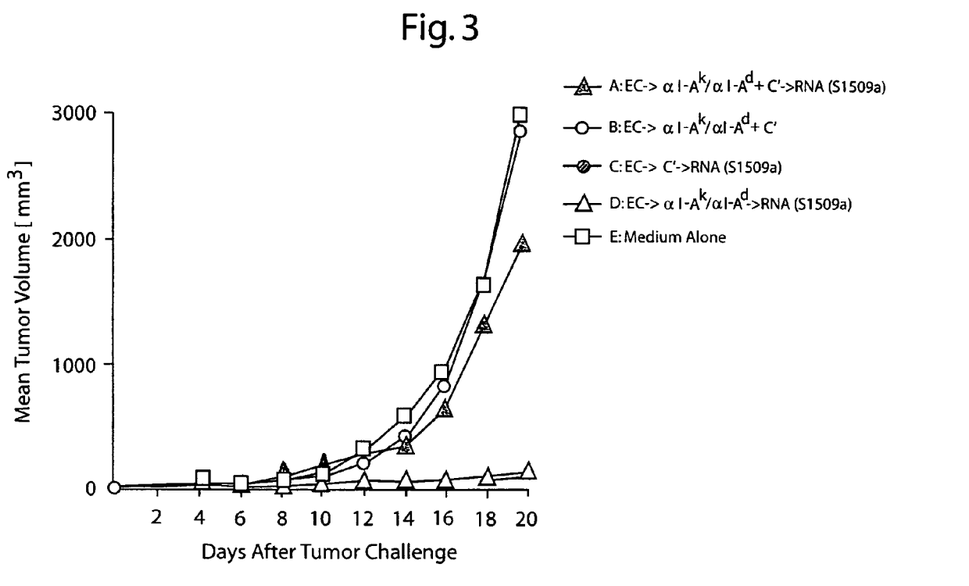
FIG. 3 is a graph illustrating the effect on tumor growth in mice immunized with EC treated with anti-I-A antibodies.

Effect of removing I-A⁺ cells from EC. In order to demonstrate that LC are necessary for induction of tumor immunity in this system, a group of mice was primed with EC from which I-A⁺ cells had been deleted utilizing antibody (anti-I-A$^d$ and anti-I-A$^k$) and complement-mediated lysis prior to pulsing with RNA. This group of mice was compared to groups of animals immunized with EC treated with antibodies alone or complement alone prior to EC pulsing. Negative control groups were immunized with I-A cell-deleted EC not pulsed with RNA or with medium alone. As shown by the data in FIG. 3, deletion of I-A⁺ cells from the EC population prevented the induction of anti-tumor immunity.

Example 2

In Vivo Immunotherapy Provides Protection

Based on the results achieved in Example 1, direct cutaneous injection of total tumor RNA was attempted. Unless indicated otherwise, the procedures are as described in Example 1.

Figure 4:
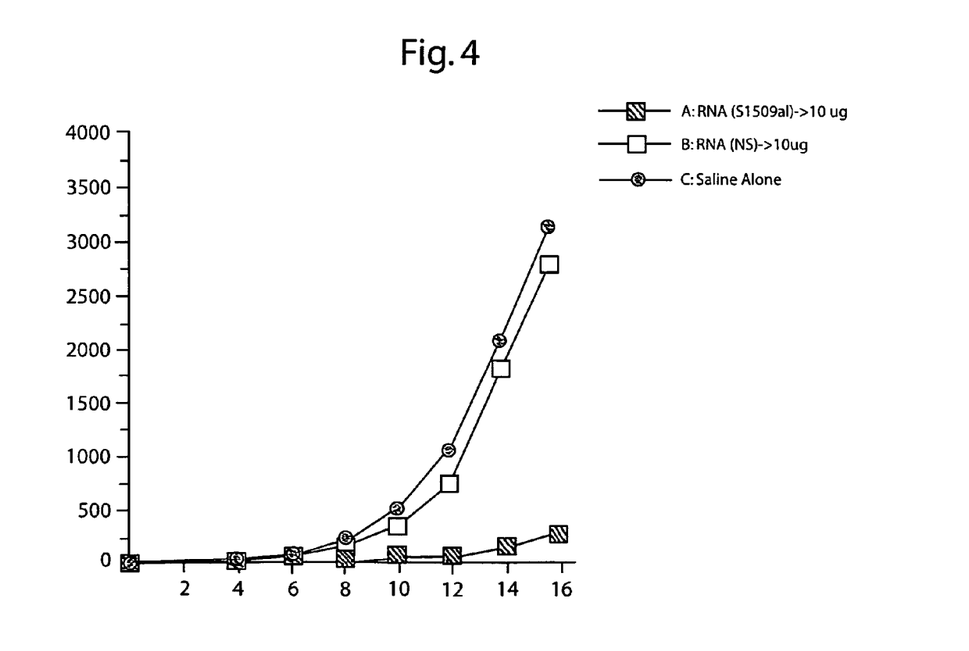
FIG. 4 is a graph illustrating the effect on tumor growth in mice immunized by direct intradermal administration of S1509a RNA. Mean tumor growth over time was measured in mice that received three consecutive intradermal injections in each flank of 10 $\mu$g per injection of total cellular RNA from the S1509a tumor (filled square), 10 $\mu$g of total cellular RNA from the NS cell line (clear square), or saline alone (circle). Mice were challenged with live S1509a tumor cells 1 week after the last immunization. N=5 in all groups. A vs. B, C: $p<0.001$.

Immunization of mice by intradermal administration of RNA. To examine whether intradermal administration of total cellular RNA from the S1509a tumor could induce anti-tumor immunity, a group of naïve CAF$_1$ mice was injected intradermally with RNA derived from the S1509a tumor. Groups of control animals were immunized with RNA derived from NS cells or with saline alone. Immunizations of 10 μg total RNA (from about 106 tumor cells) were performed a total of three times in two spots per mouse at weekly intervals, and one week after the last immunization all mice were challenged with 1×10⁶ living S1509a cells s.c. Tumor growth was then scored over time. As shown by the data in FIG. 4, mice immunized with RNA derived from S1509a cells but not with RNA derived from NS cells demonstrated immunity against challenge with living tumor cells.

Figure 5:
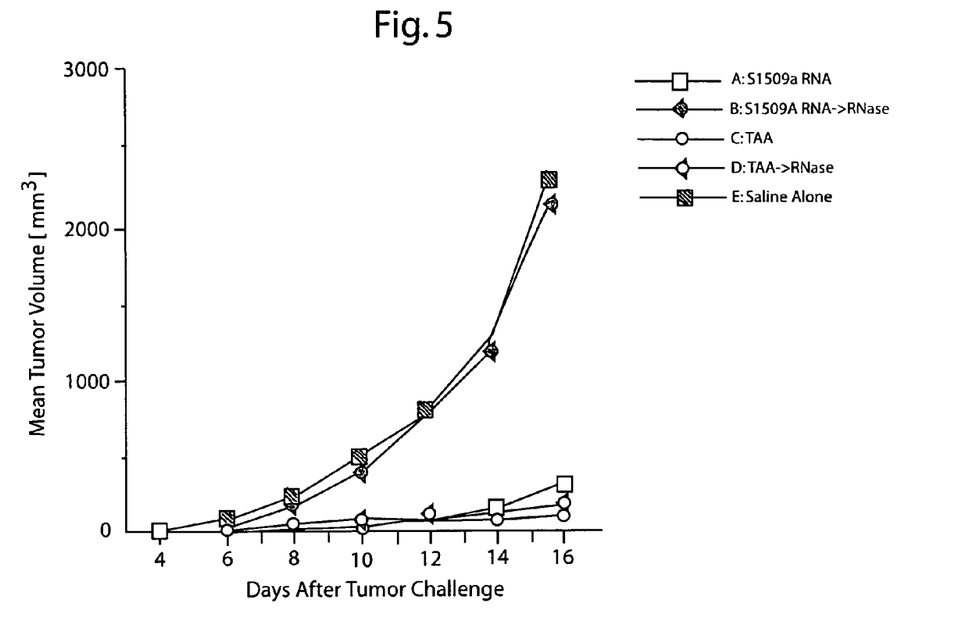
FIG. 5 is a graph illustrating the effect on tumor growth in mice immunized by intradermal immunization with RNA pretreated with RNase. Mean tumor growth over time was measured in mice that received 3 consecutive immunizations by intradermal administration of S1509a RNA clear square), S1509a RNA pretreated with RNase (filled circle), TAA (clear circle), TAA pretreated with RNase (diamond) or saline alone (filled square). N=5 in all groups. A vs. B, E: $p<0.008$. A vs. C,D: NS.

Intradermal immunization with RNA pre-treated with RNase. In order to confirm that immunity induced by intradermal administration of RNA did not result from contaminating protein antigens, a group of naïve CAF, mice was immunized with RNA pre-treated with RNase. Tumor growth in this group was compared with that in groups of mice immunized with RNA not treated with RNase, mice immunized intradermally with the TAA preparation and mice immunized intradermally with the TAA preparation pre-treated with RNase. As shown by the data in FIG. 5, mice immunized with intradermal administration of RNA, TAA, or TAA treated with RNase demonstrated good immunity against challenge with living tumor cells. However, mice immunized with RNA pre-treated with RNase failed to demonstrate immunity against the tumor.

Example 3

In Vivo Immunotherapy For Treatment

To determine whether direct cutaneous injection of total tumor RNA could inhibit or reduce growth of a tumor, groups of five mice were inoculated with living S1509a cells subcutaneously. Twenty-four hours later, the mice were immunized three times a week at twenty-four hour intervals with 10 μg of total cellular RNA from S1509a cells, total cellular RNA from the NS cell line, TAA, or medium alone. The immunization scheme was repeated every 48 hours for an additional three immunizations. Unless indicated otherwise, the procedures are as described in Example 1.

Figure 6:
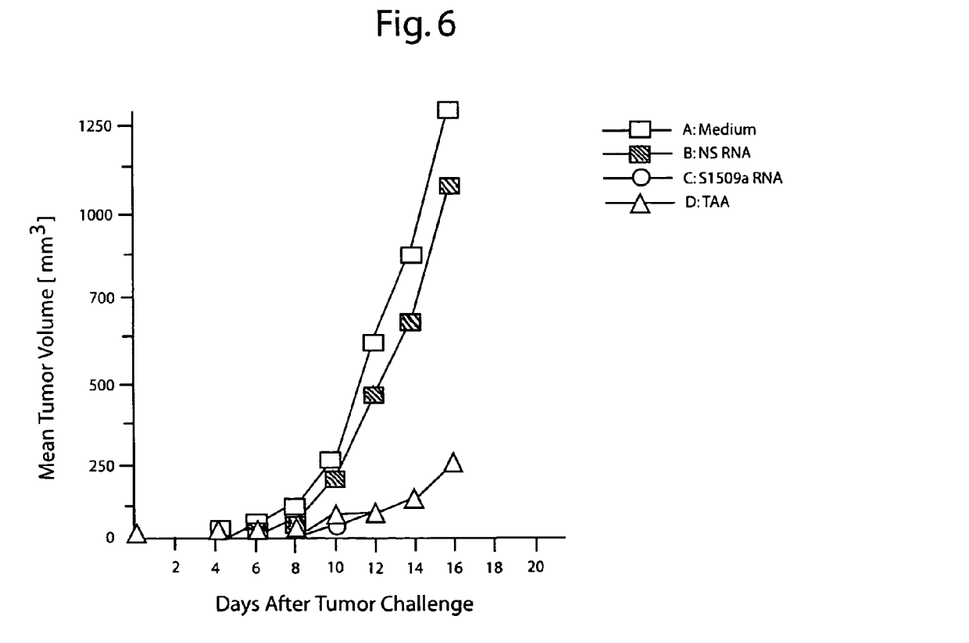

As shown in FIG. 6, tumor growth in the animals immunized with S1509a RNA and TAA was significantly inhibited compared to growth in animals immunized with NS cell RNA or medium alone. Thus, intradermal administration of tumor-derived RNA immunized against growth of the tumor from which the RNA was derived.

Example 4

Intravenous Administration of RNA Suppresses the Induction of Delayed-type Hypersensitivity (DTH) to Tumor-associated Antigens Intravenous (iv) administration of protein antigens can induce relative tolerance to subsequent immunization with that antigen. The present Example reporst that intravenous (iv) injection of RNA also reduces cell-mediated immunity to antigens encoded by the RNA utilized.

Materials and Methods

These experiments utilized the S1509 murine tumor system described in Example 1. CAF$_1$ mice (H-2$^{a/d}$) were injected with 100 μg of total cellular RNA from the S1509a spindle cell tumor line (H-2$^a$). Control animals were injected iv with saline. All mice were then immunized by subcutaneous injection of disrupted S1509a cells 3 times at 6–7 day intervals.

One week after the last injection, syngeneic epidermal cells enriched for Langerhans cell content (eEC) by antibody and complement-mediated deletion of Thy-1-bearing cells were pulsed with a soluble extract of the S1509a cells as a source of tumor-associated antigens (TAA). eEC were then thoroughly washed and 7.5×10⁵ injected into a hind footpad of each mouse. For negative controls, mice primed iv with RNA or saline aloe prior to immunization were challenged with eEC not pulsed with TAA. Twenty-four hr footpad swelling was assessed as a measure of DTH.

Results

Mice given S1509a-derived RNA demonstrated a significantly smaller DTH response (p<0.001) compared to mice primed iv with saline. In a preliminary experiment, mice primed iv with unrelated RNA (derived from the NS cell line), S1509a RNA pretreated with RNase, or saline pretreated with RNase prior to immunization failed to show a significantly inhibited DTH response compared to positive control mice primed iv with saline alone prior to immunization. These results demonstrate that iv administration of total cellular RNA from the S1509a tumor suppresses the induction of DTH to S1509a-derived TAA.

The present invention is not to be limited in scope by the specific embodiments described herein. Indeed, various modifications of the invention in addition to those described herein will become apparent to those skilled in the art from the foregoing description and the accompanying Figures. Such modifications are intended to fall within the scope of the appended claims.

It is further to be understood that all base sizes or amino acid sizes, all molecular weight or molecular mass values, quantities of RNA, and all values for suppression of tumor growth or induction of immune tolerance are approximate, and are provided for description.

All patents, patent applications, publications, and other materials cited herein are hereby incorporated herein reference in their entireties.

What is claimed is:

1. A method of inducing an immune response to a tumor in a subject, which method comprises intradermally or subcutaneously administering total tumor cell RNA to cutaneous cells of the subject in vivo, in an amount effective to elicit an immune response against the tumor, wherein the total tumor cell RNA is from tumor cells from the subject, and the immune response reduces or inhibits growth of the tumor.

2. A method for protecting a subject from a cancer, which method comprises intradermally or subcutaneously delivering an immunologically effective amount of total tumor cell RNA to cutaneous cells of the subject in vivo, wherein the total tumor cell RNA is taken from an autologous tumor associated with the cancer.

3. The method of claim 1, further comprising delivering an immunostimulatory amount of an immune activating or inflammatory cytokine to the subject.

4. The method of claim 1, wherein the tumor is a fibrosarcoma tumor.

* * * * *